United States Patent
Rayhanabad

(12)
(10) Patent No.: US 6,241,749 B1
(45) Date of Patent: Jun. 5, 2001

(54) ADJUSTABLE TENSION DEVICE FOR SUTURES

(76) Inventor: Simon B. Rayhanabad, 15691 Carousel La., Huntington, CA (US) 92649

( * ) Notice: Subject to any disclaimer, the term of this patent is extended or adjusted under 35 U.S.C. 154(b) by 0 days.

(21) Appl. No.: 09/290,458

(22) Filed: Apr. 12, 1999

(51) Int. Cl.[7] .................................................. A61B 17/04
(52) U.S. Cl. ............................................ 606/232; 606/233
(58) Field of Search .................................... 606/232, 233, 606/139, 148, 149, 150, 151, 228, 230

(56) References Cited

U.S. PATENT DOCUMENTS

| | | | |
|---|---|---|---|
| 3,695,271 | * 10/1972 | Chodorow | 128/335 |
| 4,667,675 | * 5/1987 | Davis | 128/335 |
| 5,527,341 | * 6/1996 | Gogolewski et al. | 606/232 |

* cited by examiner

*Primary Examiner*—Michael Buiz
*Assistant Examiner*—Lien Ngo
(74) *Attorney, Agent, or Firm*—William G. Lane

(57) ABSTRACT

A tension-adjusting device for sutures comprising a body through which sutures tend to be knotted at the top of the body with a plurality of flexible legs extending outwardly and downwardly from the body to rest on the body of a patient. In one embodiment, the body of the top half and the bottom half can be rotated with respect to each other to tighten the sutures passing therethrough.

23 Claims, 7 Drawing Sheets

ADJUSTABLE TENSION DEVICE FOR SUTURES

FIELD OF THE INVENTION

The present invention is directed to a medical device used in surgery. In particular, the device is a tension-adjusting device for sutures to be used in abdominal surgery and other surgeries involved in the closure of large incisions and wounds.

BACKGROUND OF THE INVENTION

Major invasive surgery, such as surgery on the trunk and the legs, require relatively large openings, i.e., openings longer than three inches. The closure of surgical openings and large holes in the trunk and legs has unique problems. Because of the articulation of the skeletal elements, muscular movement of the trunk and/or legs, and/or motion of body organs, such as the stomach, intestines, lungs, diaphragm, and the like, closure of such wounds or openings can be difficult to maintain until healed. Wounds are usually closed with sutures, surgical staples, adhesives, or a combination thereof. If a patient is active, restless or is subject to involuntary physical exertion, such as coughing, sneezing, and/or cramps, skeletal articulation, muscular movement, or organ motion can open such wounds-even those wounds which have partially healed. Such movement or exertions can cause the staples and/or the sutures to be torn out and/or the patient's skin to be torn, causing the wound to open.

It is an object of the present invention to provide a means to permit a large incision, wound, or opening to be sutured, especially an incision, wound, or opening (collectively, "wound" herein) in the trunk or leg, whereby the sutures are elastically tied to permit the trunk or leg to move, expand, and contract and yet still provide adequate tension of the sutures to maintain closure of the wound.

SUMMARY OF THE INVENTION

The present invention is directed to a tension-adjusting device for sutures and a method of closing off wounds, employing sutures using the tension-adjusting device.

The tension-adjusting device for sutures comprises a body having at least three legs extending outwardly and downwardly from the body, the body having a dorsal surface and a ventral surface, with peripheral sides connecting the dorsal surface and the ventral surface; at least two ducts, each duct having at least one opening on the dorsal surface and at least one opening on the ventral surface of the body.

The legs on at least one side of the body are partially bendable in a vertical direction. Each leg has proximal end connected to the body and a distal end; each leg has a foot at its distal end; and each foot has a sole or bottom surface to rest on the skin of the patient. Preferably, the sole of each foot on each leg has a frictional surface to restrict movement of the foot on the skin. Although the legs do not have to be the same length, preferably the feet of all the legs will rest on a common plane. In one embodiment of the invention, all the legs are same length. In another embodiment of the present invention, the legs on one side, i.e., on one half of the body, are longer than the legs on the other side or other half of the body.

Each duct can have a single opening at the dorsal surface and a single opening at the ventral surface. In another embodiment of the present invention, each duct has a plurality of openings on the ventral surface of the body. The body can have one or more grooves on its dorsal surface; preferably the duct openings on the dorsal surface open into the grooves. The sutures can ride in the grooves between the duct openings to protect the sutures or the knots tying the ends of two sutures.

In one embodiment of the present invention, the body is divided into two elements, the top element and the bottom element. The top element has a dorsal side and a bottom side and the bottom element has a top side and a ventral side. The top element has an engagement seat on its bottom side and the bottom element has an engagement seat on the top side. The engagement seat of each element is engageable in a mating relationship to form the body. The top element has a cavity opening to its bottom side, and the bottom element has a cavity opening to its top side. The engagement of the top element and bottom element forms an enclosed cavity between the bottom side of the top element and the top side of the bottom element. Alteratively, only one of the elements can have a cavity which becomes an enclosed cavity when the two elements are matingly engaged. The dorsal side of the top element constitutes the dorsal surface of the body, and the ventral side of the bottom element constitutes the ventral surface of the body.

The sutures are secured to the adjustable tension device by feeding the free end of a suture through one duct from the ventral surface and across the dorsal surface of the body to another duct and feeding the free end down through the duct from the dorsal surface or side to the ventral surface or side.

In one embodiment of the present invention, the engagement seats of the top element and the bottom element have a circular shape, and the top element is rotatably mounted on the bottom element when the two elements are engaged in a mating relationship. In this embodiment, the top element can be rotated on the bottom element permitting the sutures which are secured by the device to be rotated with the top element, thus tightening the tension of the sutures. This is accomplished because the sutures extend through the ducts in the top element and the bottom element. The top element has a plurality of ducts extending therethrough with openings on its dorsal side and bottom side, each duct having at least one opening on the dorsal side and at least one opening on the bottom side of the top element. The bottom element has a plurality of ducts extending therethrough, from its ventral side to its top side, each duct having at least one opening on the top side of the bottom element and at least one opening on the ventral side of the bottom element. Preferably, when the seats of the top element and the bottom element have circular shapes, the top element has a shaft extending downward from its bottom side, coaxial with the circular shaped seat, and the bottom element has a sleeve extending upwardly from its top side coaxial with its circular shaped seal, the shaft rotatably received within the sleeve when the top element and bottom element are matingly engaged. Alternatively, the top element can have a sleeve extending downwardly from its bottom side, coaxial with its circular shaped seat, and the bottom element can have the shaft extending upwardly from its top side coaxially with the circular shaped seat. The shaft of the bottom side is rotatably received within the sleeve of the top element when the top element and the bottom element are matingly engaged.

The ducts in the top element are coaxial with the ducts in the bottom element when the top and bottom elements are matingly engaged, and the duct openings in the bottom side of the top element and the duct openings in the top side of the bottom element are aligned or in register.

In another embodiment of the present invention, the seats of the top element and bottom element each have a shape which is symmetrical in at least two directions so that the two elements can be engaged in mating relationships with the top element positioned in either of at least two directions with respect to the bottom element. In this embodiment, the seats of the top element and the bottom element will be symmetrical in at least two directions. If the seat is rectangular or oval in shape, the top element can be rotated 180°, lifting it off the bottom element and turning it and then matingly engaging the two elements. If the engaging seats of the two elements are triangular in shape, the top element can be lifted off the bottom element and rotated in one of three directions. Similarly, if the engaging seats of the two elements have a square shape, the top element can be lifted off the bottom element, and the top element can be rotated in one of four directions and then matingly engage the bottom element again. The ducts in the top element are coaxial with the ducts in the bottom element when the top and bottom elements are matingly engaged with such elements.

In order to have room for the sutures to be stretched or pulled in the tension adjusting device when the top element is rotated with respect to the bottom element, the top element and/or the bottom element has a central cavity open to its bottom side or top side, respectively. Alternatively, or in addition, the bottom element also can have a central cavity opening to its top side. Preferably, the cavity will have a baffle upon which the sutures can wind when the elements are rotated.

In another embodiment of the present invention, the legs on one side or one half of the body are longer than the legs on the other side or other half of the body. Preferably, when such a device is in use, it is oriented so that the suture extends from the side of the device having the longer legs towards the wound In such an embodiment, the ducts can be angled towards the feet of the longer legs so that the duct openings on the ventral side of the body are closer to the long legs and optionally, the duct openings on the dorsal side of the body are closer to the short legs.

In other embodiments of the present invention, the ducts can extend approximately vertically through the body or through the first element and second element of the body, composing a top element and a bottom element. Even if the device has legs of equal length, the ducts can be angled towards one side of the body or the ducts can be arranged so that the duct openings on the ventral surface of the body are closer to one side of the body.

DETAILED DESCRIPTION OF THE INVENTION

Figure 1:
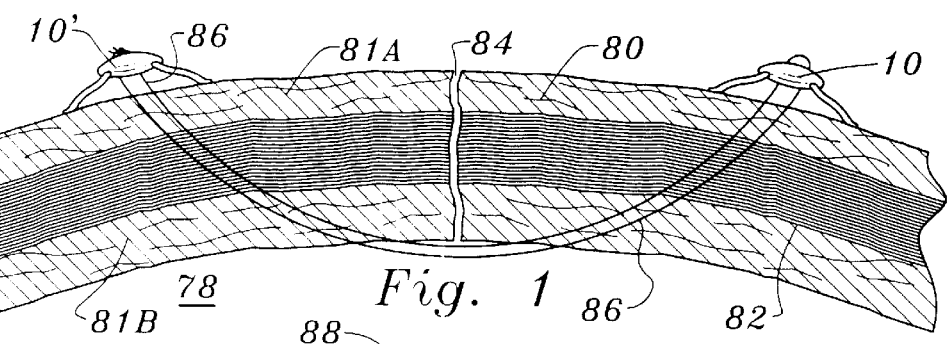
FIG. 1 is a cross-sectional view showing use of a tension-adjusting device for sutures of the present invention.

Referring to FIG. 1, a cross-sectional view of an abdominal wall 80 is shown comprising an exterior layer of connective tissue 81A separated by abdominal muscle 82 from the interior connective tissue layer 81B. The abdominal wall 80 closes off the abdominal cavity 78. A cut, wound, opening, or incision 84 (collectively, "wound" herein) has been made through the abdominal wall, either by accident, by criminal intent, or by surgical intervention. The abdominal wall is subject to a number of influences, including emotional responses of the patient; movement and action and motion of the organs, such as the stomach and the intestines; involuntary movement caused by coughing and sneezing; and voluntary movement, such as lifting, sitting upright, and the like. To prevent the wound from re-opening, sutures are extended through the abdominal wall into the abdominal cavity on one side of the incision and back up through the abdominal wall on the other side of the incision. The suture forms a large loop and is placed under tension to close off the wound. To maintain the sutures under predetermined tension and to provide for movement of the sutures because of movement of the abdominal wall, the sutures are secured to adjustable tension devices 10 for sutures. At least one pair of devices is placed on either side of the wound or incision 84 and the suture 86 is threaded through the ducts of devices 10 and 10' threaded through the abdominal wall 80 with a needle to form a large loop which is tied off with a knot 88 of device 10' into the abdominal cavity 78 and the wound 84. The suture is looped through the ducts and around the top of device 10 and threaded back through the abdominal wall, across the abdominal cavity, and wound 84, back through the abdominal wall, then to a separate duct of device 10' with knot 88. The two free ends of the suture threaded through device 10' are tied together. The surgeon adjusts the tension on the two ends of the suture prior to tying the free ends together to provide sufficient tension on the sutures to close the wound. However, the surgeon does not apply sufficient pressure so as to bend the legs 14 to the point where the ventral side of the device touches the skin. The surgeon will place sufficient tension on the sutures so as to flex the legs to a degree where the ventral surface of the devices 10 and 10' ride above the abdominal wall 80. When pressure is applied to the abdominal wall by the patient either through movement or otherwise, the abdominal wall expands placing the sutures under additional tension. The tension is absorbed by the flexible legs 14 of the devices which bend in response to the tension on the sutures. The sutures retain their tension via the devices and keep the wound closed. The devices give, through the flexible legs, permitting the suture to give in the abdominal wall, thus preventing the sutures from tearing the skin or tearing out of the skin.

Figure 2:
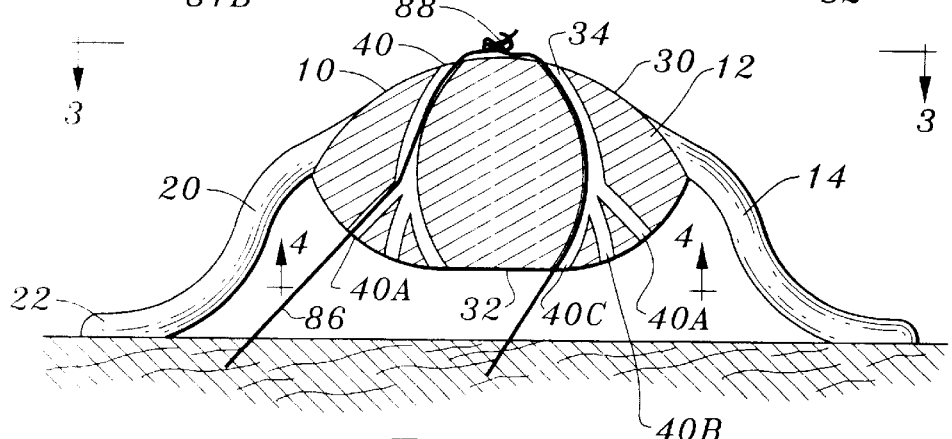
FIG. 2 is an enlarged side cross-sectional view of the tension-adjusting device of sutures for the present invention.

As shown in FIG. 2, the tension-adjusting device 10 of the present invention comprises a body 12 with a plurality of flexible legs 14. The flexible legs have flexible limbs 20 connected to a foot 22 at the distal end of the leg. The legs are secured to the body 12 at their proximal end. Extending through the body from its dorsal side 30 to its ventral side 32 are two or more ducts 34. The ducts are adapted to receive sutures. To give the surgeon more flexibility in the placement of the device, the ducts are bifurcated at the bottom of the body so that the ventral side has two or more openings 40A, 40B, and 40C in which to thread through the sutures.

The needle end of the sutures is initially threaded through the duct 34 from the dorsal side, out one of the ventral openings 40A–40C, and into the abdominal wall as described above to close off the wound. The needle end of the sutures is then returned as described above and threaded through one of the ventral openings 40A–40C through another duct 34 to the dorsal side. The ends of the sutures are tightened to provide sufficient tension on the sutures to close off the wound and the ends of the sutures are tied together with knot 88.

In FIGS. 5 through 11, the tension-adjusting device for sutures 10A has a plurality of legs 14 attached to a body 12A. The body has a removable and rotatable top half 50 and a bottom half 52. The two halves are matingly engaged to each other as will be described herein. The top half has two or more ducts 34 for receiving sutures. The ducts open on the dorsal side into a dorsal groove 36 which protects the suture as it is looped over from one duct to the other or when a knot is formed between the two free ends of a suture. The ducts open at their bottom ends into a cavity 56, which is open to the bottom side of the top half. Extending downwardly from the cavity 56 is a hollow shaft 58 which extends beyond the bottom periphery 59 of the top half. Around the bottom periphery 59 of the top half, there is a circumferential groove 60. The bottom half has ducts 34 opening to the ventral side of the bottom half and opening at their top ends into cavity 62 which is open to the top of the bottom half. A sleeve 64 extends upwardly from the cavity 62 beyond the top periphery 61 of the bottom half. The bottom half has a circumferential shoulder 66 on its top side which is adapted to engage and ride in circumferential groove 60 on the bottom side of the top half. The hollow shaft 58 of the top half and the sleeve 64 of the bottom half are coaxial with the axis of rotation 54 of the two halves. When the top half engages the bottom half, the hollow shaft 58 is received within the sleeve 64 for rotational movement. When the top half and bottom half join together, the shoulder 66 of the bottom half engages the circumferential groove 60 of the top half for rotational movement. The outer circumferential surface of the hollow shaft 58 and/or the inner circumferential surface of the sleeve 64 can have a high frictional surface and/or the surface of the circumferential groove 60 and/or the outer surface of the circumferential shoulder 62 can have a high frictional surface. The frictional surfaces can be roughened surfaces or surfaces having small teeth or protrusions molded into the surfaces. The top half 50 can be rotated on the bottom half 52 by manipulation of the hand and yet the frictional surface has a high enough coefficient friction to prevent the top half from rotating back due to tension from the sutures. The sleeve and hollow shaft act as an internal baffle about which the sutures can be wound.

Figure 3:
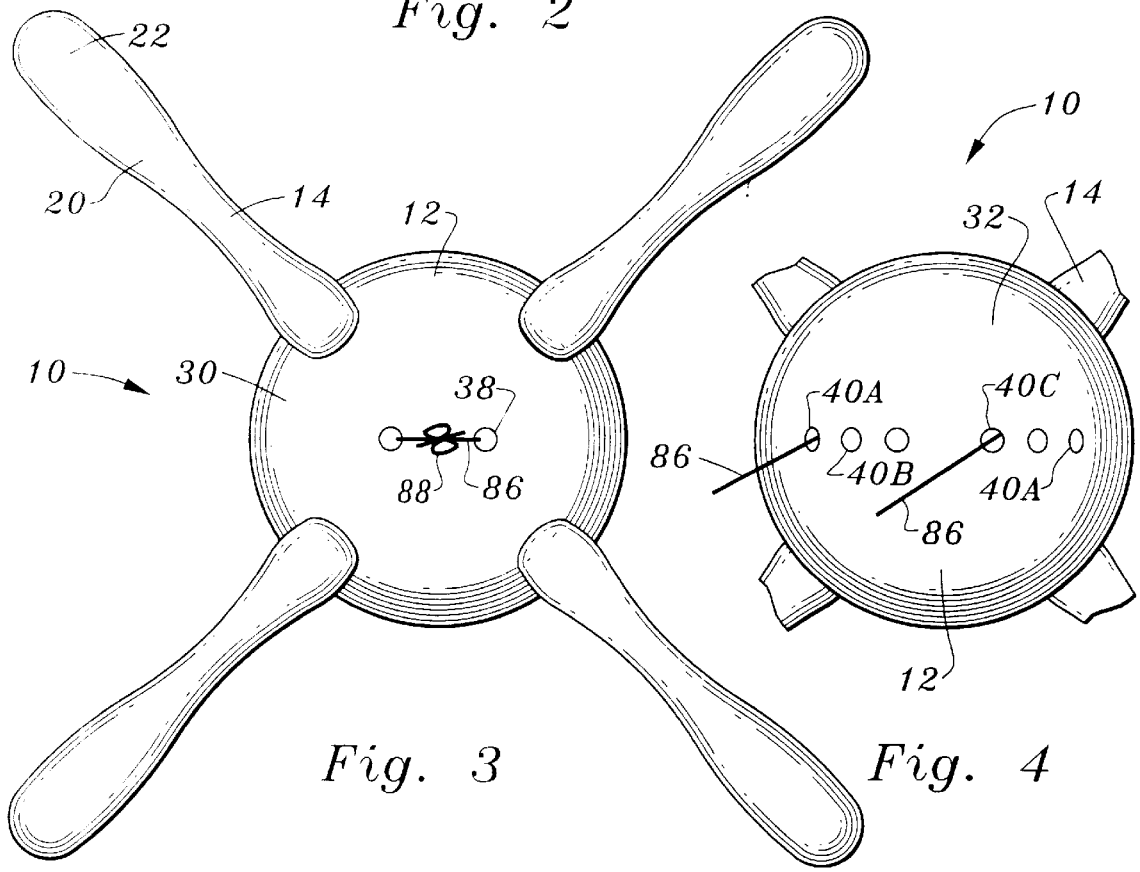
FIG. 3 is a view taken along lines 3—3 of FIG. 2.
Figure 4:
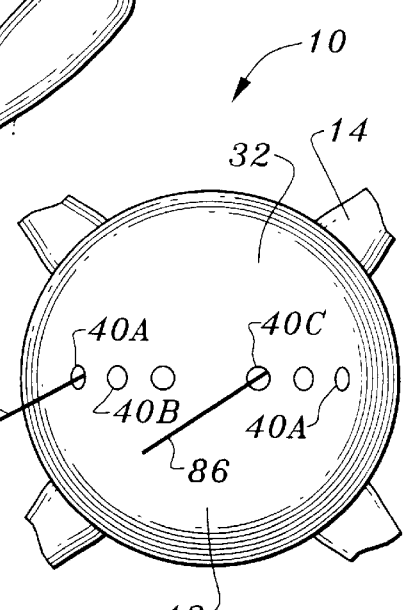
FIG. 4 is a view taken along lines 4—4 of FIG. 2.
Figure 5:
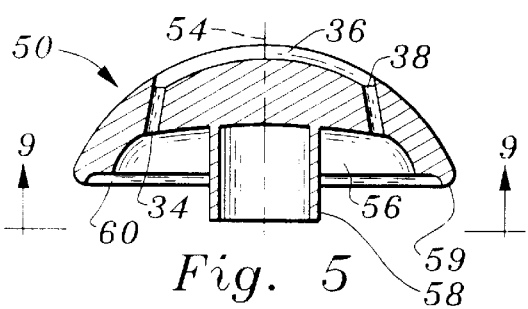
FIG. 5 is a side cross-sectional view of the top element of another embodiment of the device of the present invention shown in FIG. 7.
Figure 6:
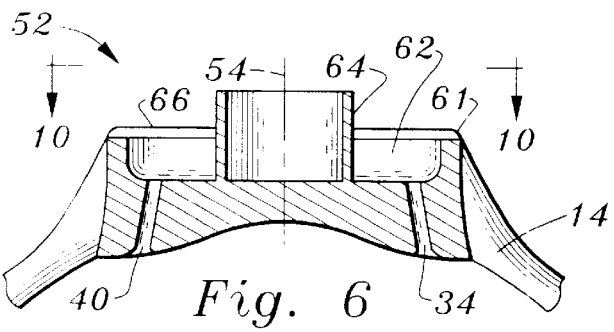
FIG. 6 is a side cross-sectional view of the bottom element of another embodiment of the device of the present invention shown in FIG. 7.
Figure 7:
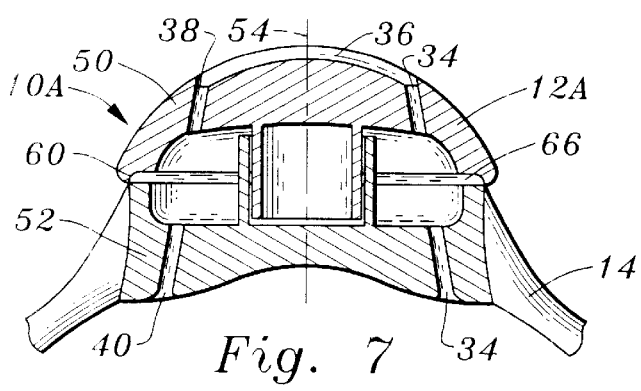
FIG. 7 is a side cross-sectional view of another embodiment of the device of the present invention.
Figure 8:
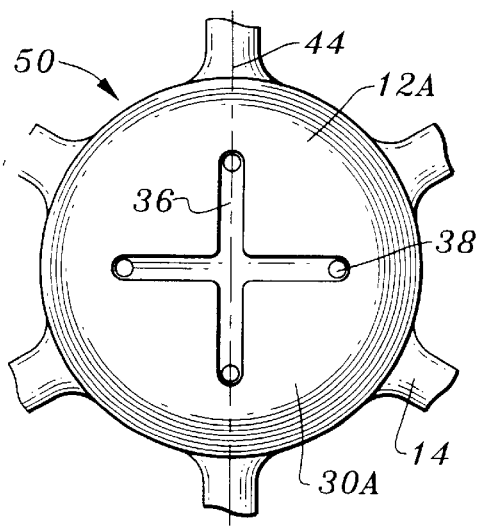
FIG. 8 is a top view of the device of FIG. 7.
Figure 9:
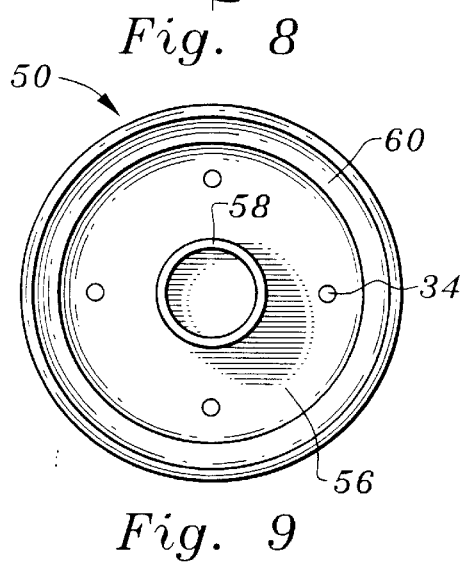
FIG. 9 is a view taken along lines 9—9 of FIG. 5.
Figure 10:
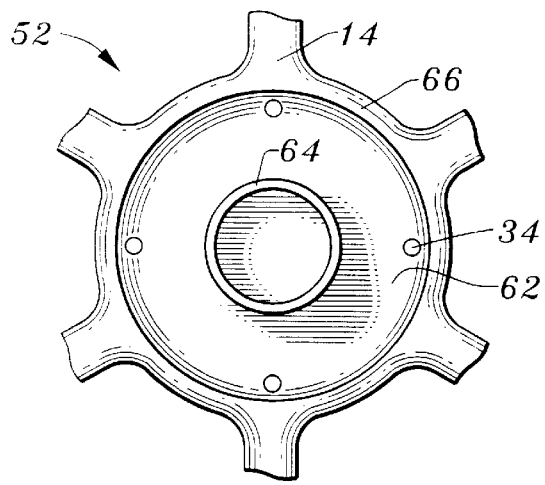
FIG. 10 is a view taken along lines 10—10 of FIG. 6.
Figure 11:
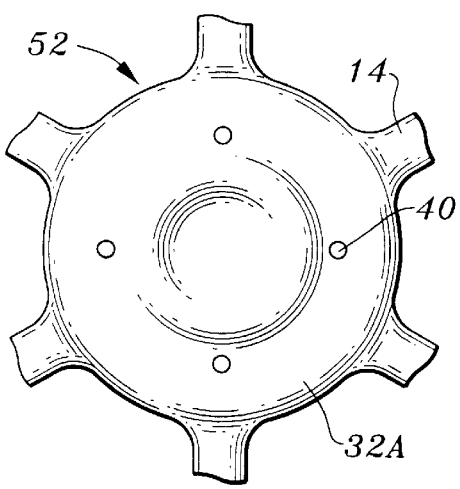
FIG. 11 is a bottom view of the device of FIG. 7.
Figure 12:
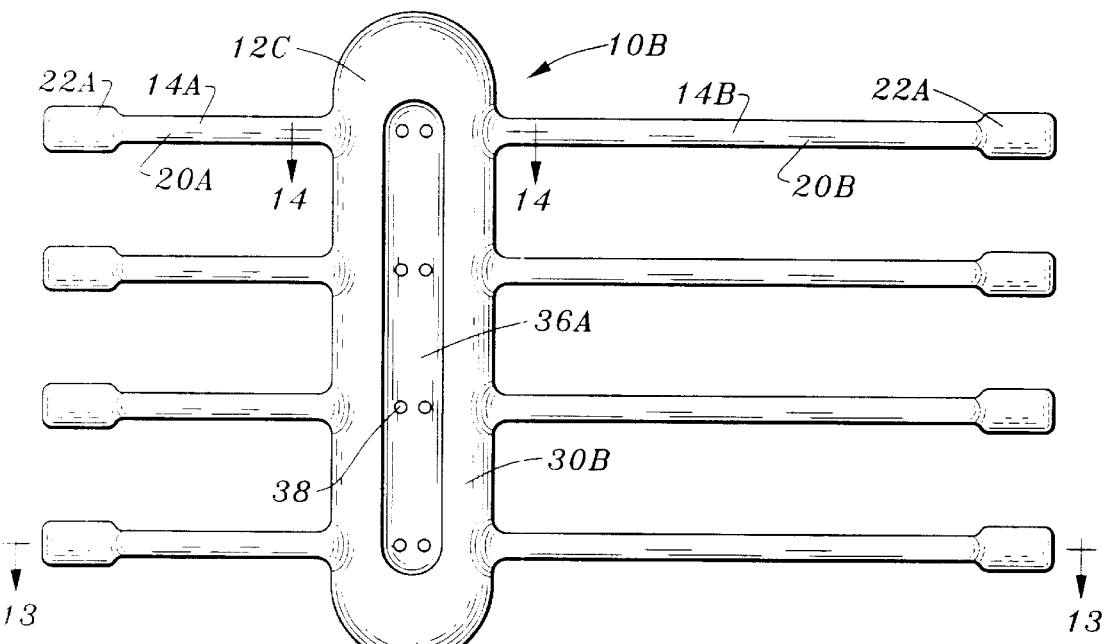
FIG. 12 is a top view of another embodiment of the device of the present invention.
Figure 13:
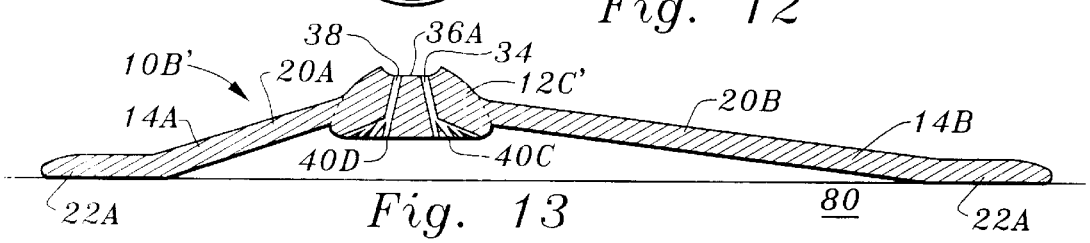
FIG. 13 is a view taken along lines 13—13 of FIG. 12.
Figure 14:
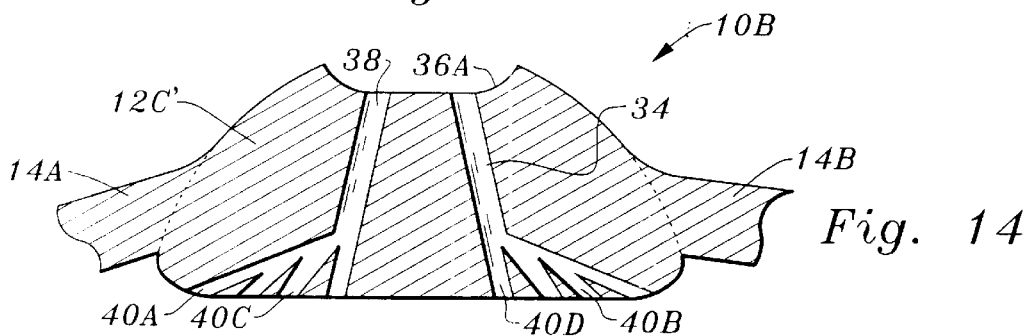
FIG. 14 is a view taken along lines 14—14 of FIG. 12.

As with device 10, shown in FIGS. 1 through 4, the suture is initially fed through one of the ducts 34 of the body 10A, i.e., through the duct 34 in the top half and through the corresponding duct 34 in the lower half. The ducts 34 of the top half are aligned with the ducts 34 of the lower half when suturing the wound. This is easily accomplished by having markings 44 on the exterior of the top half and the bottom half which, when aligned, provide that the ducts 34 of the two halves are in alignment to ease threading of the sutures through the ducts 34. The suture is threaded through the abdominal wall, through the abdominal cavity back through the abdominal wall to a similar device 10 or 10A on the other side of the wound. The suture comes back again and is threaded through the other duct 34 of the device. The tension of the suture is adjusted by the surgeon and then the two free ends of the suture are tied, as shown in FIGS. 2 and 3, with respect to device 10. If, later on, the surgeon wishes to tighten the tension of the suture, the surgeon can rotate the top half 50 with respect to the bottom half 52 to draw more of the suture into cavities 56 and 62 of the device. The suture is drawn around the exterior of the sleeve 64 as the top half is rotated to tighten the suture. As discussed above, the frictional surfaces of the circumferential groove 60 and/or the shoulder 62 and/or the outer circumferential surface of the hollow shaft 58 and/or the inner circumferential surface of the sleeve 64 inhibit back rotation of the top half with respect to the bottom half from tension of the suture, especially when tension of the suture is increased by movement of the patient or movement within the abdominal cavity.

Referring to FIGS. 12 through 15, in this embodiment of the tension-adjusting device 10B of the present invention, the device has an elongated body 12C having two sets of legs 14A and 14B extending from the longitudinal sides of the body 12C. In the embodiment shown, legs 14B are appreciably longer than legs 14A. However, the legs can be of equal length. The legs are attached at their proximal ends to the body and have feet 22A at their distal ends. The body has a longitudinal groove 36A extending along its ventral side in a longitudinal direction. The dorsal openings 38 of the ducts 34 open into the groove 36A. The ducts 34 have a plurality of ventral openings 40A–40B on the bottom end. Sutures can be threaded through the ventral opening the surgeon selects.

Figure 15:
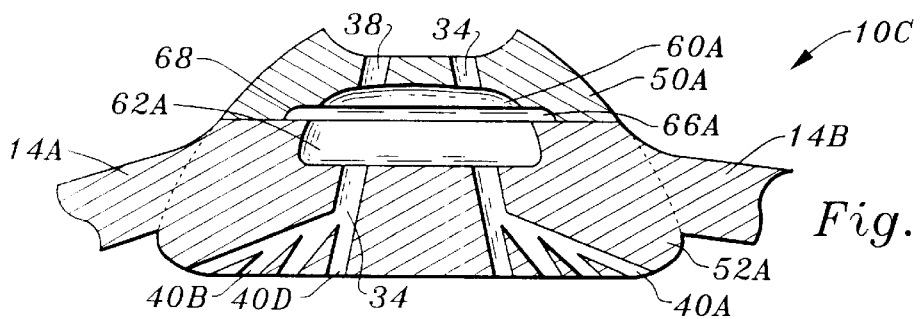
FIG. 15 is a fragmentary cross-sectional view of another embodiment of the device of FIG. 12.

Another embodiment of the tension-adjusting device 10C for sutures is illustrated in FIG. 15. Device 10C has an upper section 50A and a lower section 52A. The legs 14A and 14B extend from the side of the bottom section 52A. The top section 50A has ducts 34 opening into cavity 60A which opens to the bottom side of the top section 50A. The ducts 34 of the bottom section 52A open into cavity 62A which opens to the top side of bottom section 52A. The bottom side of the top half 50A has a groove 60A on its inner perimeter and the bottom half 52A has a shoulder 66A running about its inner perimeter, which is adapted to be received by and engaged by the groove 60A.

Preferably, the bottom feet 22A on the longer leg 14B have a frictional surface to prevent sliding of the device across the skin when in use. Optionally, the feet 22A on the shorter legs 14A also can have a frictional surface. The device 10C is positioned so that the longer legs 14B face the wound.

The legs 14B and 14A are flexible so that when the sutures are placed under additional tension from body movement or the like, the legs can bend, permitting the body of the device to come closer to the skin, thus giving some slack to the sutures to prevent tearing which occurs without use of the device.

Figure 16:
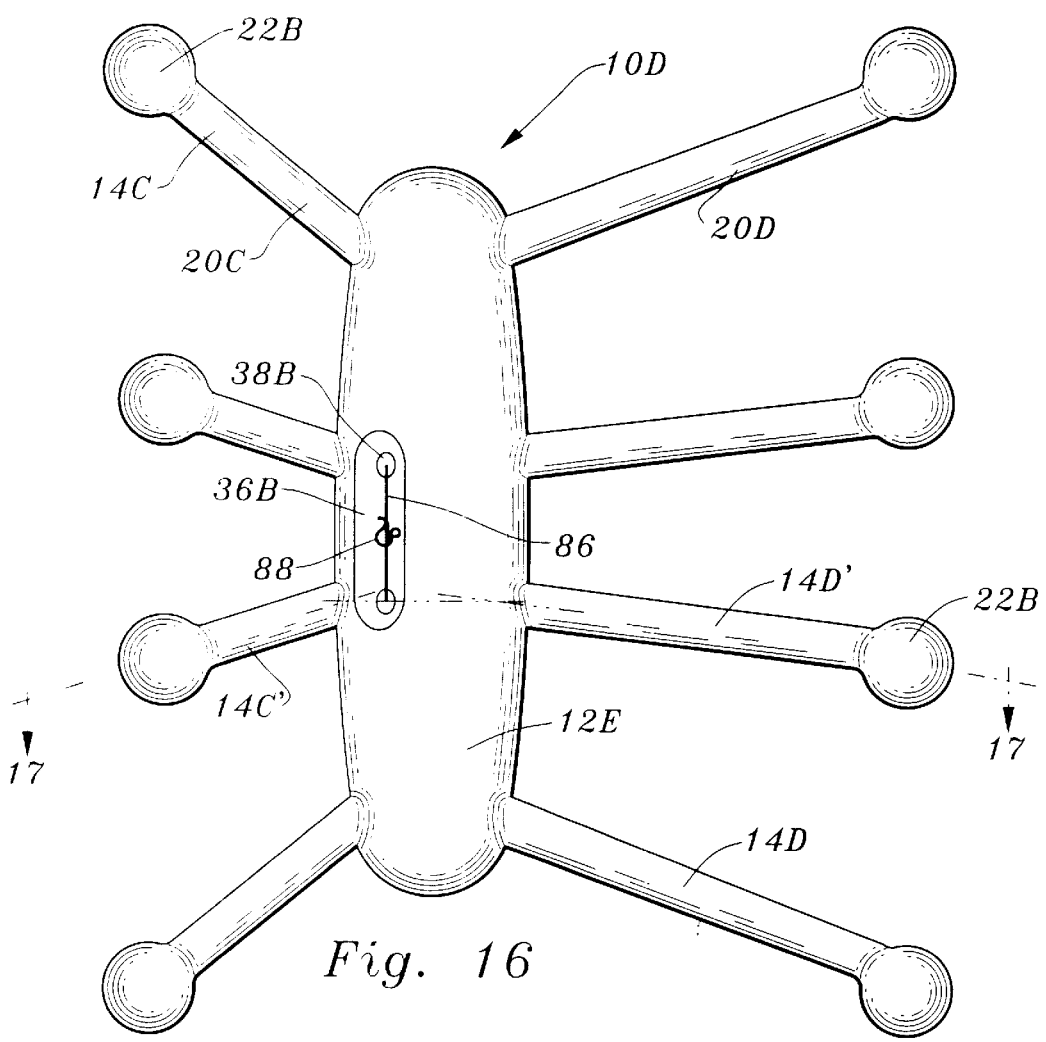
FIG. 16 is a top view of another embodiment of the device of the present invention.
Figure 17:
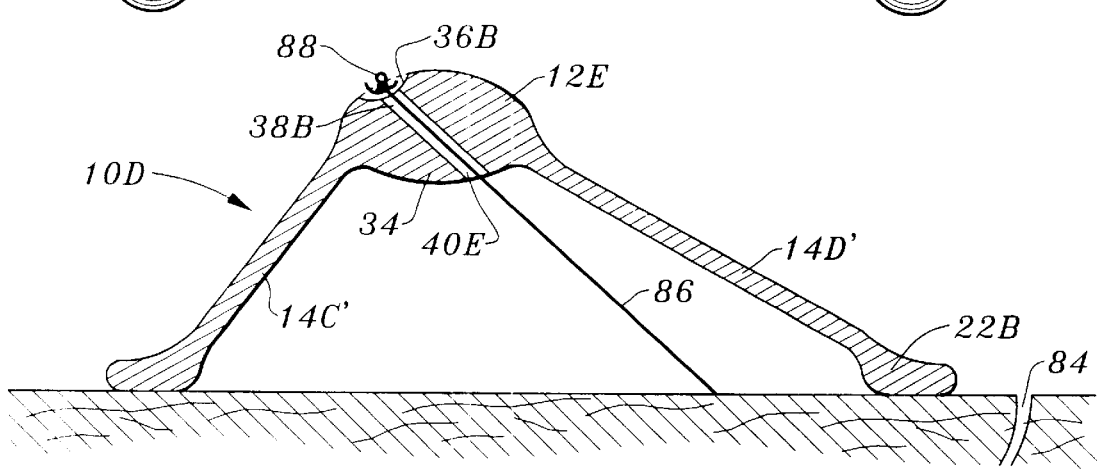
FIG. 17 is a side cross-sectional view taken along lines 17—17 of FIG. 16.

Referring to FIGS. 16 and 17, the tension-adjusting device 10D for sutures comprises an elongated body having a plurality of legs 14D and 14C. The legs 14C are longer than the two middle legs 14C'. Similarly, 14D are longer than the legs 14D' in the middle. The legs on one side of the body can be the same length or different lengths. In addition, the middle legs can be longer than the outer legs. The legs can also be the same length.

The body has a small groove 36B for sutures. The two ducts 34 through the body have their dorsal openings 38B opening into the groove 36B. The ducts are angled with the ventral opening 40E being closer to the longer legs 14D'. The dorsal opening 38B of the ducts are closer to legs 14C. Preferably the bottom surfaces or soles of the feet 22B of the longer legs 14D have a high frictional surface to prevent sliding of the device on the surface of the skin. This device is used when a more angular tension is to be applied to the sutures. The longer legs 14D are positioned towards the wound 84 with the duct 34 at an angle in the direction of the longer legs 14D and 14D'. A suture 86 is threaded through one duct 34, threaded through the abdominal wall through the abdominal cavity past the wound or incision up through the abdominal wall to a similar device 10, 10A, 10B, or 10C on the other side of the wound and then the suture is passed through a return duct on the other device back through the abdominal wall, abdominal cavity, and the abdominal wall back into the other duct of device 10D. The surgeon places the appropriate tension on the free ends of the suture to close the wound and then ties the two free ends of the suture 86 together to form knot 88. Because of the frictional soles of feet 22B and the angle of the duct 34, the suture can exit the abdominal wall 80 at an angle to apply more angular tension to the sutures. Although the device 10D is shown with only two ducts 34, the device can be fitted with two ducts, four ducts, six ducts and the like.

Figure 18:
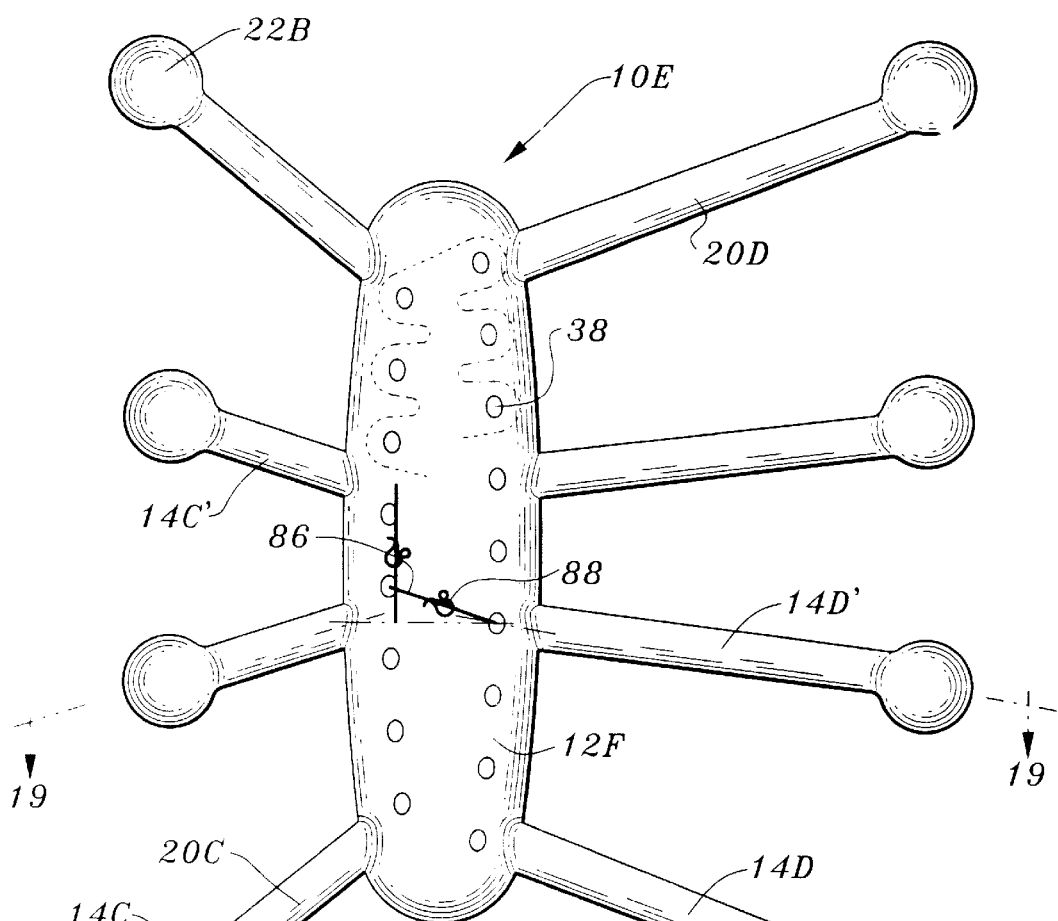
FIG. 18 is a top view of another embodiment of the device of the present invention.
Figure 19:
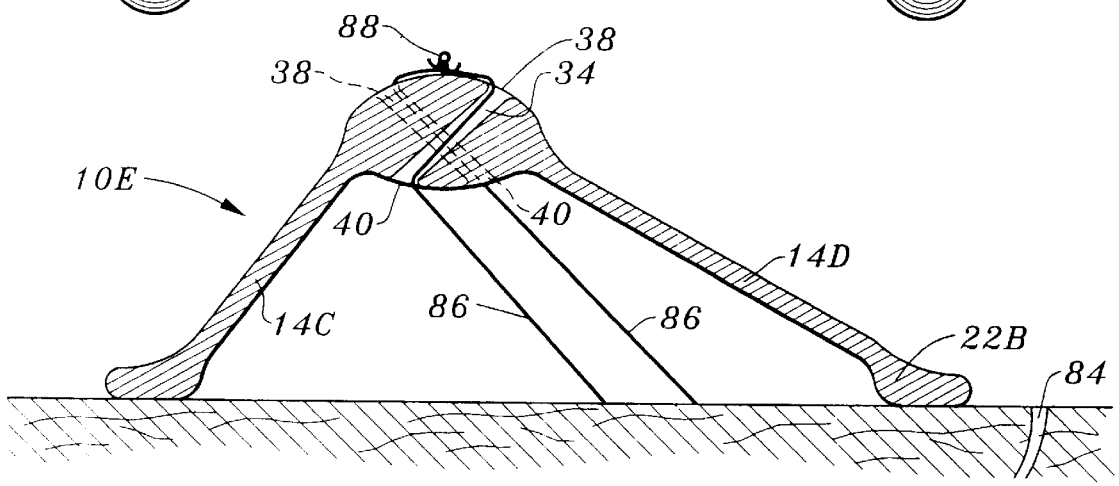
FIG. 19 is a side cross-sectional view taken along lines 19—19 of FIG. 18.

Referring to FIGS. 18 and 19, the tension-adjusting device for sutures 10E has an elongated body shape and legs 14C, 14C', 14D, and 14D', similar to that of the device 10D illustrated in FIGS. 16 and 17. The device 10E has one principal difference from 10D; the ducts 34 are positioned in two rows on either longitudinal side of the body with the openings of the ducts on one row positioned midway between the openings of the ducts on the other row. The ducts in the row closest to the shorter legs 14C and 14C' are angled towards the longer legs 14D and 14D' so that the ventral openings of these ducts are closer to the longer legs. The dorsal openings closer to the longer legs are angled towards the shorter legs so that the ventral openings of these ducts are closer to the shorter legs 14C and 14C'. Sutures are threaded through one of the ducts and then sewed through the abdominal wall in the abdominal cavity, through the abdominal wall on the other side of the wound 84, threaded through a device similar to 10E on the other side of the wound or incision, passed over the device, and then sewed back through the abdominal wall through the abdominal cavity, back through the abdominal wall on the other side of the incision, and threaded through another duct angled in an opposite direction of device 10E. The two free ends of the suture are tightened by the surgeon and then tied to form knot 88, as described above. The dorsal openings 38 of the ducts can open into a zigzag groove connecting all the openings (as shown in phantom).

Figure 20:
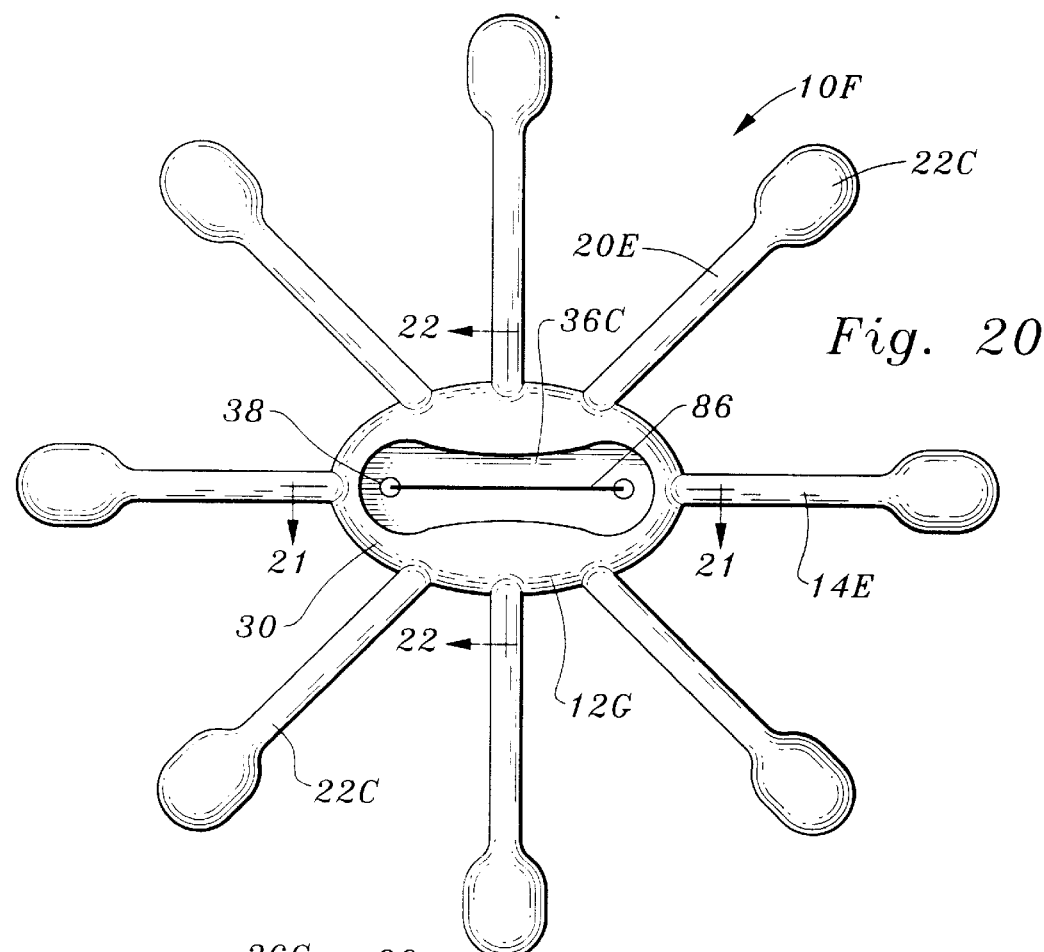
FIG. 20 is a top view of another embodiment of the present invention.
Figure 21:
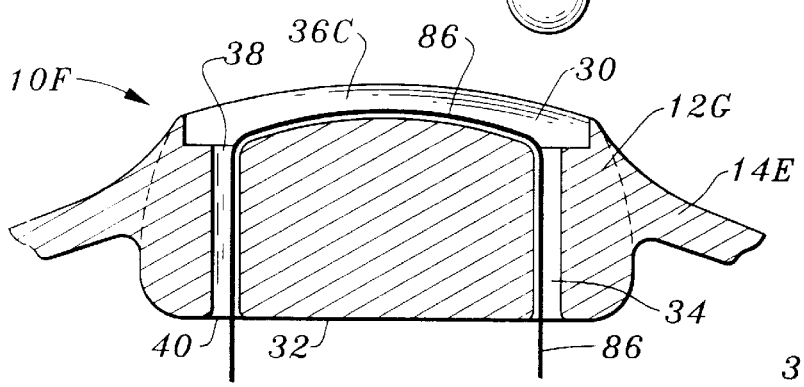
FIG. 21 is a side cross-sectional view taken along lines 21—21 of FIG. 20.
Figure 22:
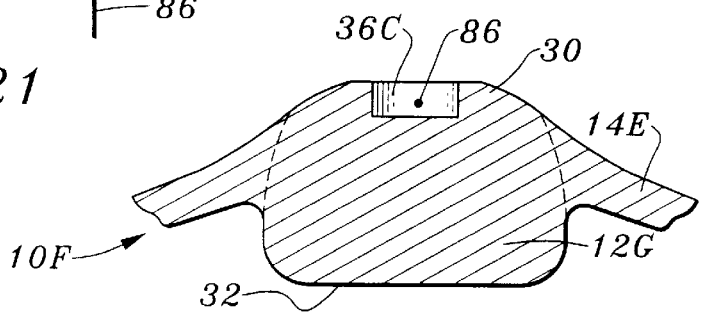
FIG. 22 is a side partial cross-sectional view taken along lines 22—22 of FIG. 20.

Referring to FIGS. 20–22, the tension-adjusting device for sutures 10F comprises a body 12G with legs 14E. The legs are of equal length and have limbs 20C and feet 22C. The body is oval shaped and has a large dorsal groove 36C through which the ducts 34 open into. The ducts extend to the ventral side of the body and open on the ventral side through ventral openings 40. The legs maintain the body above the skin of the patient. The limbs of leg 22C are flexible and provide for the tension adjustment of the sutures, when tension is applied to the sutures from body movement and the like.

Figure 24:
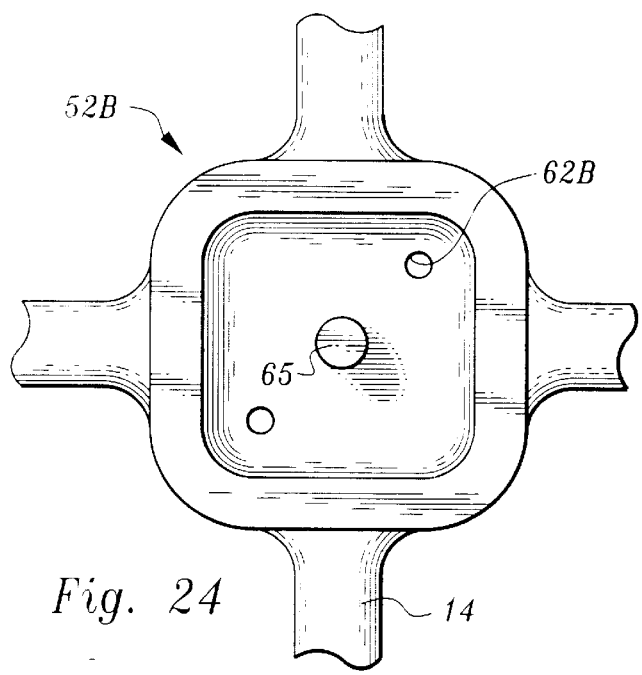
FIG. 24 is a top view taken along lines 24—24 of FIG. 23.
Figure 25:
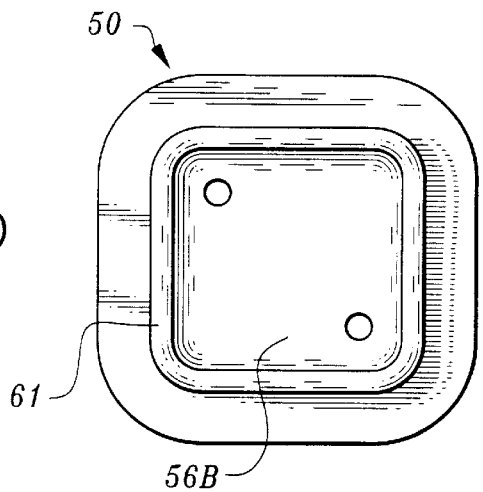
FIG. 25 is a bottom view taken along lines 25—25 of FIG. 23.
Figure 23:
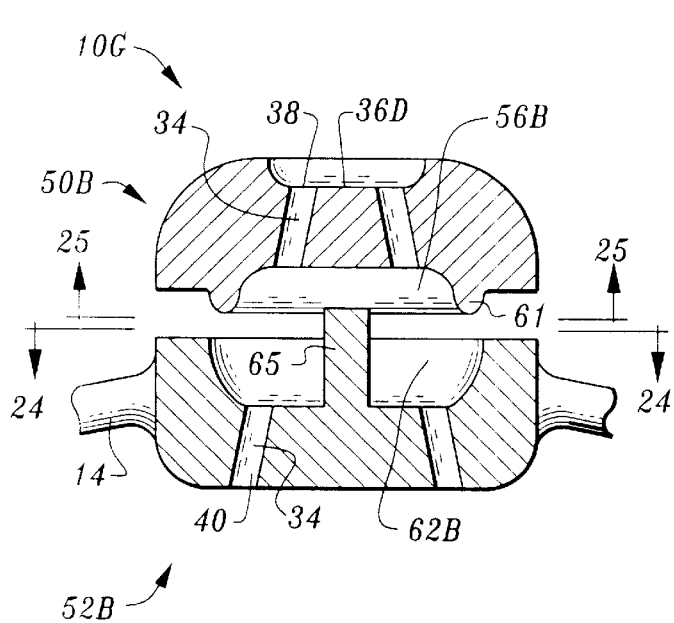
FIG. 23 is a side partial cross-sectional view of another embodiment of the device of the present invention.

Referring to FIGS. 23–25, the tension-adjusting device for sutures 10G comprises a plurality of legs 14 and a body comprising a top half 50B and a lower half 52B. The two halves are adapted to be matingly engaged in a fashion similar to that of device 10A illustrated in FIGS. 5–11. The legs extend from the side of the bottom half 52B. The bottom half 52B is roughly square in cross section, having four side walls and four legs, one leg extending from each of the four sides of the bottom half. The top half has two ducts 34 having openings into cavity 56B on its ventral side and openings 38 opening into groove 36D on its ventral side. The bottom half has ducts 34 opening on its ventral side with ventral openings 40 and opening on its top side into cavity 62B. The top half has a perimeter ring wall 61 which is adapted to enter into and seat in cavity 62B so that the top half and bottom half can matingly engage. A shaft or baffle 65 extends up from the cavity 62B of the lower half, about which the sutures can wind, in the event the surgeon wishes to tighten the tension on the sutures. The tension on the sutures is tightened by lifting the top half of the device 52B and twisting it a one quarter turn or one half turn and then dropping the top half back down into the lower half so that the perimeter ring wall 61 seats in the cavity 62B.

Figure 26:
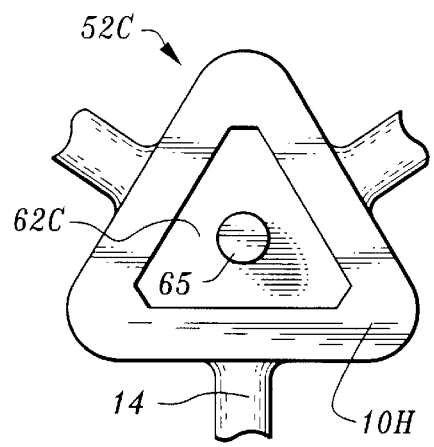
FIG. 26 is a top view similar to FIG. 24 of another embodiment of the device of the present invention.

Referring to FIG. 26, FIG. 26 shows the bottom half of a tension-adjusting device for sutures 10H. This illustrates that the shape of the body of the device can have one of a number of shapes, including triangular shape, hexagonal shape, octagonal shape, rectangular shape, square shape, oval shape, round shape, and the like. The lower half 52C of the device 10H has the legs 14 extending from its three sides. The bottom half has a cavity 62C which opens to its top. A shaft 65 or baffle extends upward from the cavity 62C, about which sutures can be twisted if the surgeon wishes to adjust the tension of the sutures. The top half (not shown) has a similar shape to the bottom half and can have a ring perimeter or wall similar to perimeter ring wall 61 of the device illustrated in FIGS. 23–25, which engages the wall of cavity 62C to seat the top half to the bottom half 52C.

Although the invention has been illustrated with specific embodiments, the intent of the invention is to provide a device which permits adjustment of suture tension by re-knotting or rotating the top half of the device and automatic maintenance of suture tension during body movement, motion or action via the flexible legs to maintain wound or incision closure and to provide a means to permit the sutures to move through the tissue by having a device take up play when the body expands or contracts or has other actions.

I claim:

1. A tension-adjusting device for sutures comprising a body and at least three legs extending outwardly and downwardly from the body, the body having a dorsal side and a ventral side and at least two ducts extending from the dorsal side to the ventral side, each duct having at least one opening on the dorsal side and at least one opening on the ventral side of the body, each leg having a limb, a proximal end connected to the body, and a distal end which is connected to a foot, the feet of all the legs positioned below the ventral side of the body; the legs on at least one side of the body being partially bendable in the vertical direction.

2. The device according to claim 1 wherein all the legs are at least partially bendable in the vertical direction.

3. The device according to claim 2 wherein each leg terminates with a foot at its distal end, each foot having a sole.

4. The device according to claim 3 wherein the sole of each foot has a frictional surface.

5. The device according to claim 2 wherein each duct has a plurality of openings on the ventral side of the body.

6. The device according to claim 5 wherein the body has a groove on its dorsal side and at least the opening for two of the ducts open into the groove.

7. The device according to claim 2 wherein the openings of the ducts on the dorsal side of the body are in pairs and the dorsal side of the body has at least one groove having openings of the paired ducts in the dorsal side of the body open into the groove.

8. The device according to claim 2 wherein the body has a groove on its dorsal side and all of the dorsal openings of the ducts on the dorsal side of the body open in the groove.

9. The device according to claim 1 wherein the body has a top element and a bottom element, the top element having a seat on its bottom side and the bottom element having a seat on its top side, the seats of the two elements engaging in a mating relationship to form the body and to form a closed cavity therebetween, the top element having a top side and bottom side and at least two ducts extending therethrough, each duct having at least one opening on the top side and at least one opening on the bottom side, the bottom element having a top side and a bottom side, the bottom element having at least two ducts, each duct having at least one opening on the top side and at least one opening on the bottom side.

10. The device according to claim 9 wherein the seats of the top element and bottom element have a circular shape and the seats have frictional surfaces, the top element rotatable on the bottom element on their seats.

11. The device according to claim 10 wherein the top element has a shaft extending downward from its bottom side coaxial with the circular shaped seat, and the bottom element has a sleeve extending upwardly from its top side, coaxial with its circular shaped seat, the shaft rotatably received within the sleeve when the top element and the bottom element are matingly engaged.

12. The device according to claim 10 wherein the top element has a shaft extending downward from its bottom side coaxial with the circular shaped seat, and the bottom element has a shaft extending upwardly from its top side, coaxial with its circular shaped seat, the shaft rotatably received within the sleeve when the top element and the bottom element are matingly engaged.

13. The device according to claim 10 wherein the ducts in the top element are coaxial with the ducts in the bottom element, when the top elements are matingly engaged and the openings of the ducts in the bottom side of the top element and the openings of the ducts in the top side of the bottom element are in register.

14. The device according to claim 10 wherein the seats of the top element and the bottom element have a shape which is symmetrical in at least two directions so that the two elements can be engaged in a mating relationship with the top element positioned in either of one of at least two directions with respect to the bottom element.

15. The device according to claim 14 wherein the ducts in the top element are coaxial with the ducts in the bottom element when the top and bottom elements are matingly engaged.

16. The device according to claim 9 wherein the top element has a cavity opening solely to its bottom side.

17. The device according to claim 9 wherein the bottom element has a cavity opening solely to its top side.

18. The device according to claim 2 wherein the legs on one side of the body are longer than the legs on the other side of the body.

19. The device according to claim 18 wherein the ducts are angled towards the feet of the longer legs so that the duct openings on the ventral side of the body are closer to the long legs.

20. The device according to claim 19 wherein the duct openings on the dorsal side are closer to the shorter legs.

21. The device according to claim 2 wherein the ducts extend approximately vertically downwards to the body.

22. The device according to claim 2 wherein the ducts are angled towards one side the body.

23. The device according to claim 2 wherein the duct openings on the ventral surface are closer to one side of the body.

* * * * *